(12) United States Patent
Anderson et al.

US007786346B2

(10) Patent No.: US 7,786,346 B2
(45) Date of Patent: *Aug. 31, 2010

(54) GENERATION OF PLANTS WITH IMPROVED DROUGHT TOLERANCE

(75) Inventors: Catherine Anderson, Durham, NC (US); Stephen Aaron Lee, Durham, NC (US); Kerrie Powell, Durham, NC (US); Pilar Puente, Durham, NC (US); Jennifer Lee Rhein, Raleigh, NC (US); Philip Reid Timmons, Durham, NC (US); Vincent Paul Mary Wingate, Chapel Hill, NC (US)

(73) Assignee: Agrinomics LLC, Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/163,394

(22) Filed: Jun. 27, 2008

(65) Prior Publication Data

US 2009/0126043 A1 May 14, 2009

Related U.S. Application Data

(63) Continuation of application No. 10/697,787, filed on Oct. 29, 2003, now abandoned.

(60) Provisional application No. 60/482,076, filed on Jun. 24, 2003.

(51) Int. Cl.
*A01H 1/00* (2006.01)
*A01H 5/00* (2006.01)
*C12N 15/09* (2006.01)
*C12N 15/82* (2006.01)

(52) U.S. Cl. .................... 800/278; 800/298; 435/430.1; 435/468

(58) Field of Classification Search ........................ None
See application file for complete search history.

(56) References Cited

U.S. PATENT DOCUMENTS

| 5,939,601 | A | 8/1999 | Klessing et al. |
| 5,981,842 | A | 11/1999 | Wu et al. |
| 6,057,490 | A | 5/2000 | Ryals et al. |
| 6,417,428 | B1 | 7/2002 | Thomashow et al. |
| 6,664,446 | B2 | 12/2003 | Heard et al. |
| 6,791,012 | B1 | 9/2004 | Chen et al. |
| 7,521,592 | B2 * | 4/2009 | Federspiel et al. .......... 800/279 |
| 2002/0160378 | A1 | 10/2002 | Harper et al. |

FOREIGN PATENT DOCUMENTS

| WO | WO 96/31608 | 10/1996 |
| WO | WO 02/16655 | 2/2002 |
| WO | WO 03/091412 | 11/2003 |

OTHER PUBLICATIONS

Aarts et al., "Different requirements for *EDS1* and *NDR1* by disease resistance genes define at least two R gene-mediated signaling pathways in *Arabidopsis*," *Proc Natl. Acad. Sci. USA*, 95:10306-10311, 1998.
Aasland et al., "The SANT domain: a putative DNA-binding domain in the SWI-SNF and ADA complexes, the transcriptional co-repressor N-CoR and TFIIIB," *Trends BioChem, Sci.*, 21:87-88, 1996.
Alvim et al., "Enhanced Accumulation of BiP in Transgenic Plants Confer Tolerance to Water Stress" *Plant Physiol.*, 126:1042-1054, 2001.
Asai et al., "MAP kinase signaling cascade in *Arabidopsis* innate immunity," *Nature*, 415:977-983, 2002.
Bennetzen and Jones, "Approaches and Progress in the Molecular Cloning of Plant Disease Resistance Genes," *Genetic Engineering*, 14:99-124, 1992.
Berrocal-Lobo et al., "Constitutive expression of Ethylene-Response-Factor1 in *Arabidopsis* confers resistance to several necrotrophic fungi," *The Plant Journal*, 29(1):23-32, 2002.
Bowling et al., "A mutation in *Arabidopsis* that leads to constitutive expression of systemic acquired resistance," *Plant Cell*, 6:1845-1857, 1994.
Bowling et al., "The *cpr5* mutant of *Arabidopsis* expresses both NPR1-dependent and NPR1-independent resistance," *Plant Cell*, 9:1573-1584, 1997.
Cao et al., "Effect of two conserved amino acid residues on DREB1A function," *Biochemistry (Mosc).*, 66(6):623-627, 2001.
Cao et al., "Generation of broad-spectrum disease resistance by overexpression of an essential regulatory gene in systemic acquired resistance," *Proc. Natl. Acad. Sci. USA*, 95:6531-6536, 1998.
Chen et al., "Expression profile matrix of *Arabidopsis* transcription factor genes suggests their putative functions in response to environmental stresses," *The Plant Cell*, 14(3):559-574, 2002.
Clarke et al., "Constitutive disease resistance requires *EDS1* in the *Arabidopsis* mutants *cpr1* and *cpr6* and is partially *EDS1* -dependent in *cpr5*," *The Plant Journal*, 26:409-420, 2001.
Clarke et al., "Roles of salicylic acid, jasmonic acid, and ethylene in cpr-induced resistance in *Arabidopsis*," *The Plant Cell*, 12:2175-2190, 2000.
Clarke et al., "Uncoupling PR gene expression from NPR1 and bacterial resistance: characterization of the dominant *Arabidopsis cpr6-1* mutant," *The Plant Cell*, 10:557-569, 1998.
Dangl and Jones, "Plant pathogens and integrated defense responses to infection," *Nature*, 411:826-833, 2001.
Delaney et al., "*Arabidopsis* signal transduction mutant defective in chemically and biologically induced disease resistance," *Proc. Natl. Acad. Sci. USA*, 92:6602-6606, 1995.
Devadas et al., "The *Arabidopsis hrl1* mutation reveals novel overlapping roles for salicylic acid, jasmonic acid and ethylene signalling in cell death and defence against pathogens," *The Plant Journal*, 30(4):467-480, 2002.
Dewdney et al., "Three unique mutants of *Arabidopsis* identify *eds* loci required for limiting growth of a biotrophic fungal pathogen," *The Plant Journal*, 24(2):205-218, 2000.

(Continued)

*Primary Examiner*—Medina A Ibrahim
(74) *Attorney, Agent, or Firm*—Klarquist Sparkman, LLP.

(57) ABSTRACT

The present invention is directed to plants that display a pathogen resistance and increased drought tolerance phenotype due to altered expression of a PRDT1 nucleic acid. The invention is further directed to methods of generating plants with a pathogen resistance and increased drought tolerance phenotype.

13 Claims, No Drawings

OTHER PUBLICATIONS

Feys and Parker, "Interplay of signaling pathways in plant disease resistance," *TIG*, 16(10):449-455, 2000.

Frye and Innes, "An *Arabidopsis* mutant with enhanced resistance to powdery mildew," *The Plant Cell*, 10:947-956, 1998.

GenBank Accession No. AAM63284, "ethylene response factor ERF1 [*Arabidopsis thaliana*]," 1 page, 2003.

GenBank Accession No. AAN32899, "transcription factor TSRF1 [*Lycopersicon esculentum*]," 2 pages, 2002.

GenBank Accession No. AAN77067, "ethylene responsive element binding protein [*Lycopersicon esculentum*]," 1 page, 2002.

GenBank Accession No. B84718, "RPCI11-27L6.TV RPCI-11 *Homo sapiens* genomic clone RPCI-11-27L6, genomic survey sequence," 1 page, 1998.

GenBank Accession No. BAC21534, "putative ethylene response factor ERF1 [*Oryza sativa* Japonica Group]," 1 page, 2002.

GenBank Accession No. CAB88324, "DNA binding protein [*Arabidopsis thaliana*]," 1 page, 2000.

GenBank Accession No. NP_180681, "ethylene response factor, putative; protein id: At2g31230.1, supported by cDNA: gi_17979407, supported by cDNA: gi_20465982 [*Arabidopsis thaliana*]," 2 pages, 2002.

GenBank Accession No. NP_188965, "Human c-myc-P64 mRNA, initiating from promoter P0, (HLmyc3.1) partial cds," 2 pages, 1996.

GenBank GI No. 12331602, "*Arabidopsis thaliana* chromosome 1 BAC F22H5 genomic sequence, complete sequence," 22 pages, 2001.

Glazebrook, Jane, "Genes controlling expression of defense responses in *Arabidopsis*," *Current Opinion in Plant Biology*, 2:280-286, 1999.

Glazebrook, Jane, "Genes controlling expressions of defense responses in *Arabidopsis*—2001 status," *Current Opinion in Plant Biology*, 4:301-308, 2001.

Gu et al., "Tomato transcription factors Pti4, Pti5, and Pti6 activate defense responses when expressed in *Arabidopsis*," *The Plant Cell*, 14:817-831, 2002.

Heath. Michéle C., "Nonhost resistance and nonspecific plant defenses," *Current Opinion in Plant Biology*, 3:315-319, 2000.

Kachroo et al., "A fatty acid desaturase modulates the activation of defense signaling pathways in plants," *PNAS*, 98:9448-9453, 2001.

Kim and Delaney, "*Arabidopsis* SON1 is an F-box protein that regulates a novel induced defense response independent of both salicylic acid and systemic acquired resistance," *The Plant Cell*, 14:1469-1482, 2002.

Kim and Delaney, "Over-expression of *TGA5*, which encodes a bZIP transcription factor that interacts with NIM1/NPR1, confers SAR-independent resistance in *Arabidopsis thaliana* to *Peronospora parasitica*," *Plant J.*, 32:151-163, 2002.

Kinkema et al., "Nuclear localization of NPR1 is required for activation of *PR* gene expression," *The Plant Cell*, 12:2339-2350, 2000.

Lin et al., "*Arabidopsis thaliana* chromosome 1 BAC F22H5 genomic sequence, complete sequence," Genbank accession No. ACO25814, 2001, (retrieved Jan. 14, 2005).

Lorenzo et al., "Ethylene Response Factor1 integrates signals from ethylene and jasmonate pathways in plant defense," *The Plant Cell*, 15(1):165-178, 2003.

Lucht et al., "Pathogen stress increases somatic recombination frequency in *Arabidopsis*," *Nature Genetics*, 30:311-314, 2002.

Mach et al., "The *Arabidopsis*-accelerated cell death gene *ACD2* encodes red chlorophyll catabolite reductase and suppresses the spread of disease symptoms," *Proc. Natl. Acad. Sci. USA*, 98(2):771-776, 2001.

Maldonado et al., "A putative lipid transfer protein involved in systemic resistance signaling in *Arabidopsis*," *Nature*, 419:399-403, 2002.

Maleck et al., "Isolation and characterization of broad-spectrum disease-resistant *Arabidopsis* mutants," *Genetics*, 160:1661-1671, 2002.

Mcdowell et al., "Downy mildew (*Peronospora parasitica*) resistance genes in *Arabidopsis* vary in functional requirements for *NDR1*, *EDS1*, *NPR1* and salicylic acid accumulation," *Plant J.*, 22:523-529, 2000.

Molina et al., "Inhibition of protoporphyrinogen oxidase expression in *Arabidopsis* causes a lesion-mimic phenotype that induces systemic acquired resistance," *The Plant Journal*, 17(6):667-678, 1999.

Morel and Dangl, "Suppressors of the *Arabidopsis lsd5* cell death mutation identify genes involved in regulating disease resistance responses," *Genetics*, 151:305-319, 1999.

Nürnberger and Scheel, "Signal transmission in the plant immune response," *TRENDS in Plant Science*, 6(8):372-379, 2001.

Onate-Sanchez and Singh, "Identification of *Arabidopsis* ethylene-responsive element binding factors with distinct induction kinetics after pathogen infection," *Plant Physiology*, 128(4):1313-1322, 2002.

Papi et al., "Identifications and Disruption of an *Arabidopsis* Zinc Finger Gene Controlling Seed Germination," *Genes Dev.*, 14:28-33, 2000.

Petersen et al., "*Arabidopsis* MAP kinase 4 negatively regulates systemic acquired resistance," *Cell*, 103:1111-1120, 2000.

Reymond and Farmer, "Jasmonate and salicylate as global signals for defense gene expression," *Current Opinion in Plant Biology*, 1:404-411, 1998.

Romeis, Tina, "Protein kinases in the plant defence response," *Current Opinion in Plant Biology*, 4:407-411, 2001.

Rushton et al., "Synthetic plant promoters containing defined regulatory elements provide novel insights into pathogen- and wound inducing signaling," *Plant Cell*, 14:749-762, 2002.

Rustérucci et al., "The disease resistance signaling components *EDS1* and *PAD4* are essential regulators of the cell death pathway controlled by *LSD1* in *Arabidopsis*," *The Plant Cell*, 13:2211-2224, 2001.

Ryan et al., Accession No. T01350. EMBL database, 6 pages, 1999.

Schulze-Lefert and Vogel, "Closing the ranks to attack by powdery mildew," *Trends in Plant Science Reviews*, 5(8):343-348, 2000.

Shah et al., "A recessive mutation in the *Arabidopsis SSI2* gene confers SA- and *NPR1*-independent expression of PR genes and resistance against bacterial and oomycete pathogens," *The Plant Journal*, 25(5):563-574, 2001.

Solano et al., "Nuclear events in ethylene signaling: a transcriptional cascade mediated by Ethylene-Insensitive3 and Ethylene-Response-Factor1," *Genes and Development*, 12:3703-3714, 1998.

Stone et al., "Simulation of fungal-mediated cell death by fumonisin B1 and selection of fumonisin B1-resistant (*fbr*) *Arabidopsis* mutants," *The Plant Cell*, 12:1811-1822, 2000.

Takemoto et al., "GFP-tagging of cell components reveals the dynamics of subcellular re-organization in response to infection of *Arabidopsis* by oomycete pathogens," *Plant J.*, 33:775-792, 2003.

Tang and Innes, "Overexpression of a kinase-deficient form of the *EDR1* gene enhances powdery mildew resistance and ethylene-induced senescence in *Arabidopsis*," *The Plant Journal*, 32:975-983, 2002.

Theologis et al. "Sequence and analysis of chromosome 1 of the plant *Arabidopsis thaliana*," *Nature*, 408:816-820, 2000.

Tierens et al., "*Esa1*, an *Arabidopsis* mutant with enhanced susceptibility to a range of necrotrophic fungal pathogens, shows a distorted induction of defense responses by reactive oxygen generating compounds," *The Plant Journal*, 29(2):131-140, 2002.

Tör et al., "*Arabidopsis* SGT1b is required for defense signaling conferred by several downy mildew resistance genes," *Plant Cell*, 14:993-1003, 2002.

Tornero and Dangl, "A high-throughput method for quantifying growth of phytopathogenic bacteria *Arabidopsis thaliana*," *The Plant Journal*, 28(4):475-481, 2001.

Vogel and Somerville, "Isolation and characterization of powdery mildew-resistant *Arabidopsis* mutants," *Proc. Natl. Acad. Sci. USA*, 97(4):1897-1902, 2000.

Weymann et al., "Suppression and restoration of lesion formation in *Arabidopsis lsd* mutants," *Plant Cell*, 7:2013-2022, 1995.

Xie et al., "COI1: An *Arabidopsis* gene required for Jasmonate-regulated defense and fertility," *Science*, 280:1091-1094, 1998.

Xu et al., "The $SCF^{COI1}$ ubiquitin-ligase complexes are required for jasmonate response in *Arabidopsis*," *The Plant Cell*, 14:1919-1935, 2002.

Yanagisawa, S., "Dof DNA-Binding Proteins Contain a Novel Zinc Finger Motif," *Trends Plant Sci.*, 1(7):213-214, 1996.

Yanagisawa, S., "The Dof family of plant transcription factors" *Trends Plant Sci.*, 7:555-560, 2002.

Yang et al., "Activation of a mitogen-activated protein kinase pathway is involved in disease resistance in tobacco," *Proc Natl Acad Sci USA*, 98(2):741-746, 2001.

Yoshioka et al., "Environmentally sensitive, SA-dependent defense responses in the *cpr22* mutant of *Arabidopsis*," *The Plant Journal*, 26(4):447-459, 2001.

Zhang et al., "Interaction of NPR1 with basic leucine zipper protein transcription factors that bind sequences required for salicylic acid induction of the *PR-1* gene," *Proc Natl Acad Sci USA*, 96:6523-6528, 1999.

Zhang et al., "Interactions Between Distinct Types of DNA Binding Proteins Enhance Binding to ocs Element Promoter Sequences," *Plant Cell*, 7:2241-2252, 1995.

Zimmerli et al., "Potentiation pathogen-specific defense mechanisms in *Arabidopsis* by β-aminobutyric acid," *Proc Natl Acad Sci USA*, 97:12920-12925, 2000.

* cited by examiner

US 7,786,346 B2

GENERATION OF PLANTS WITH IMPROVED DROUGHT TOLERANCE

RELATED APPLICATIONS

This is a continuation of U.S. application Ser. No. 10/697,787, filed Oct. 29, 2003 (now abandoned), which in turn claims the benefit of U.S. provisional patent application No. 60/482,076, filed Jun. 24, 2003, the contents of both of which are incorporated herein by reference.

BACKGROUND OF THE INVENTION

Crop production is affected by numerous environmental factors. Attempts to improve crop yield under stress conditions by plant breeding have been largely unsuccessful, primarily due to the multigenic origin of the adaptive responses (Barkla et al. 1999, Adv Exp Med Biol 464:77-89). Consequently, an increasing amount of research has been dedicated to developing transgenic plants that show increased tolerance to various environmental stresses. For example, transgenic plants have been described having resistance to a broad range of plant pathogens (Stuiver and Custers, 2001, Nature 411:865-8; Melchers and Stuiver, 2000, Curr Opin Plant Biol 3:147-52; Rommens and Kishore, 2000, Curr Opin Biotechnol 11:120-5; and Mourgues et al. 1998, Trends Biotechnol 16:203-10). Transgenic plants displaying increased drought tolerance have also been described (Laporte et al. 2002, J Exp Bot 53:699-705; Qin et al. 2002, Plant Physiol 128:544-51; and Iuchi et al. 2001, Plant J 27:325-33).

Activation tagging in plants is a method of generating random mutations by insertion of a heterologous nucleic acid construct comprising regulatory sequences (e.g., an enhancer) into a plant genome. The regulatory sequences can act to enhance transcription of one or more native plant genes. Accordingly, activation tagging is a fruitful method for generating gain-of-function, generally dominant mutants (Hayashi et al., Science (1992) 258: 1350-1353; Weigel et al., Plant Physiology (2000) 122:1003-1013). The inserted construct provides a molecular tag for rapid identification of a native plant gene whose mis-expression causes a mutant phenotype of interest (e.g. drought tolerance or pathogen resistance).

SUMMARY OF THE INVENTION

The invention provides a transgenic plant comprising a plant transformation vector comprising a nucleotide sequence that encodes or is complementary to a sequence that encodes a PRDT1 polypeptide or an ortholog thereof. The transgenic plant is characterized by having increased resistance to pathogens and increased drought tolerance.

The present invention further provides a method of producing an altered pathogen resistance and drought tolerance phenotype in a plant. The method comprises introducing into plant progenitor cells a vector comprising a nucleotide sequence that encodes or is complementary to a sequence encoding a PRDT1 polypeptide or an ortholog thereof and growing a transgenic plant that expresses the nucleotide sequence. In one embodiment, the PRDT1 polypeptide has at least 50% sequence identity to the amino acid sequence presented in SEQ ID NO:2 and comprises a SANT domain. In other embodiments, the PRDT1 polypeptide has at least 80% or 90% sequence identity to or has the amino acid sequence presented in SEQ ID NO:2.

The invention further provides plants and plant parts obtained by the methods described herein.

DETAILED DESCRIPTION OF THE INVENTION

Identification of Plants with a PRDT1 Phenotype

We used activation tagging in Arabidopsis (Weigel et al, supra) to generate a large collection of transgenic plants, and tested the plants to identify those that display a phenotype of interest. Briefly, and as further described in the Examples, a large number of Arabidopsis plants were mutated with the pSKI015 vector, which comprises a T-DNA from the Ti plasmid of Agrobacterium tumefaciens, a viral enhancer element, and a selectable marker gene. When the T-DNA inserts into the genome of transformed plants, the enhancer element can cause up-regulation genes in the vicinity, generally within about 10 kilobase (kb) of the insertion. T1 plants were exposed to the selective agent in order to specifically recover transformed plants that expressed the selectable marker and therefore harbored T-DNA insertions. Seed from transformed plants were planted, and grown under various environmental stress conditions to identify plants having enhanced ability to survive the stress condition.

We discovered a transgenic plant line that exhibits increased tolerance to drought conditions. Another plant line was identified that exhibits increased resistance to the plant pathogen, P. parasitica. An analysis of the genomic DNA sequence flanking the T-DNA insertions in each of the identified lines suggested that the same Arabidopsis gene, having TAIR designation At1g75250 (GenBank Identifier No. 18410812), which encodes a myb-related protein, was associated with the drought tolerance phenotype in the one line, and the pathogen resistance phenotype in the other line. We refer to this gene herein as "PRDT1" (for Pathogen Resistant Drought Tolerant). Accordingly, in one aspect of the invention, PRDT1 genes and/or polypeptides may be employed in the development of transgenic plants having an "altered pathogen resistance phenotype", meaning that there is a detectable change in the response of the transgenic plant to pathogenic infection, compared to the similar, but non-modified plant. The phenotype may be apparent in the plant itself (e.g., in growth, viability or particular tissue morphology of the plant) or may be apparent in the ability of the pathogen to proliferate on and/or infect the plant. As used herein, "improved pathogen resistance" refers to increased resistance to a pathogen.

In another aspect of the invention the PRDT1 gene/polypeptide may be used to generate transgenic plants having an "altered drought tolerance phenotype", meaning that there is a detectable change in the ability of the transgenic plant to withstand low-water conditions compared to the similar, but non-modified plant. In general, improved (increased) drought tolerance phenotypes (i.e., ability to a plant to survive in low-water conditions that would normally be deleterious to a plant) are of interest.

A further aspect of the invention is directed to transgenic plants having a "PRDT1 phenotype" in which the plants exhibit both an increased pathogen resistance phenotype and a drought tolerance phenotype, relative to wild type plants, wherein the plants comprise a plant transformation vector comprising a nucleotide sequence that encodes or is complementary to a sequence that encodes a PRDT1 polypeptide.

As used herein, the term "transgenic plant" refers to a plant that comprises a heterologous polynucleotide within its genome. Preferably, the polynucleotide is stably integrated into the genome, such that it is passed on to successive generations. A plant cell, tissue, organ, or any other plant part into which the heterologous polynucleotides have been introduced is considered "transformed", "transfected", or "transgenic". Direct and indirect progeny of transformed plants or plant cells that also contain the heterologous polynucleotide are also considered transgenic. A "heterologous polynucleotide" is a sequence that is not native to the plant cell in which it is expressed. When used to describe a control sequence (e.g. promoter or enhancer), the term "heterologous" refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The class of plants which can be used in the methods of the present invention is generally as broad as the class of higher plants amenable to transformation techniques, including both monocotyledenous and dicotyledenous plants.

PRDT1 genes may be used in the generation of crops and/or other plant species that have improved ability to survive in low-water conditions, and improved resistance to infection by *P. parasitica* and other oomycetes and may also be useful the generation of plants with improved resistance to fungal, bacterial, and/or other pathogens. Mis-expression of PRDT1 genes may thus reduce the need for fungicides and/or pesticides.

PRDT1 Nucleic Acids and Polypeptides

*Arabidopsis* PRDT1 nucleic acid (coding) sequence is provided in SEQ ID NO:1 and in GenBank entry GI 12331602, nucleotides 20955-21335 (designated F22H5.3 and At1g75250). The corresponding protein sequence is provided in SEQ ID NO:2 and in GI 10092271.

As used herein, the term "PRDT1 polypeptide" refers to a full-length PRDT1 protein or a fragment, derivative (variant), or ortholog thereof that is "functionally active," meaning that the protein fragment, derivative, or ortholog exhibits one or more or the functional activities associated with the polypeptide of SEQ ID NO:2. In one preferred embodiment, a functionally active PRDT1 polypeptide causes an altered pathogen resistance and drought tolerance phenotype when mis-expressed in a plant. In a further preferred embodiment, mis-expression of the functionally active PRDT1 polypeptide causes increased resistance to *P. parasitica* and/or other oomycetes and increased drought tolerance. In another embodiment, a functionally active PRDT1 polypeptide is capable of rescuing defective (including deficient) endogenous PRDT1 activity when expressed in a plant or in plant cells; the rescuing polypeptide may be from the same or from a different species as that with defective activity. In another embodiment, a functionally active fragment of a full length PRDT1 polypeptide (i.e., a native polypeptide having the sequence of SEQ ID NO:2 or a naturally occurring ortholog thereof) retains one of more of the biological properties associated with the full-length PRDT1 polypeptide, such as signaling activity, binding activity, catalytic activity, or cellular or extra-cellular localizing activity. Some preferred PRDT1 polypeptides display DNA binding activity. A PRDT1 fragment preferably comprises a PRDT1 domain, such as a C- or N-terminal or catalytic domain, among others, and preferably comprises at least 10, preferably at least 20, more preferably at least 25, and most preferably at least 50 contiguous amino acids of a PRDT1 protein. Functional domains can be identified using the PFAM program (Bateman A et al., 1999 Nucleic Acids Res 27:260-262; website at pfam.wust1.edu). A preferred PRDT1 fragment comprises a SANT domain (SM00395) identified by PFAM, at approximately amino acids 8-60. Functionally active variants of full-length PRDT1 polypeptides or fragments thereof include polypeptides with amino acid insertions, deletions, or substitutions that retain one of more of the biological properties associated with the full-length PRDT1 polypeptide. In some cases, variants are generated that change the post-translational processing of a PRDT1 polypeptide. For instance, variants may have altered protein transport or protein localization characteristics or altered protein half-life compared to the native polypeptide.

As used herein, the term "PRDT1 nucleic acid" encompasses nucleic acids with the sequence provided in or complementary to the sequence provided in SEQ ID NO:1, as well as functionally active fragments, derivatives, or orthologs thereof. A PRDT1 nucleic acid of this invention may be DNA, derived from genomic DNA or cDNA, or RNA.

In one embodiment, a functionally active PRDT1 nucleic acid encodes or is complementary to a nucleic acid that encodes a functionally active PRDT1 polypeptide. Included within this definition is genomic DNA that serves as a template for a primary RNA transcript (i.e., an mRNA precursor) that requires processing, such as splicing, before encoding the functionally active PRDT1 polypeptide. A PRDT1 nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed PRDT1 polypeptide, or an intermediate form. A PRDT1 polynucleotide can also include heterologous coding sequences, for example, sequences that encode a marker included to facilitate the purification of the fused polypeptide, or a transformation marker.

In another embodiment, a functionally active PRDT1 nucleic acid is capable of being used in the generation of loss-of-function pathogen resistance or drought tolerance phenotypes, for instance, via antisense suppression, co-suppression, etc.

In one preferred embodiment, a PRDT1 nucleic acid used in the methods of this invention comprises a nucleic acid sequence that encodes or is complementary to a sequence that encodes a PRDT1 polypeptide having at least 50%, 60%, 70%, 75%, 80%, 85%, 90%, 95% or more sequence identity to the polypeptide sequence presented in SEQ ID NO:2.

In another embodiment a PRDT1 polypeptide of the invention comprises a polypeptide sequence with at least 50% or 60% identity to the PRDT1 polypeptide sequence of SEQ ID NO:2, and may have at least 70%, 80%, 85%, 90% or 95% or more sequence identity to the PRDT1 polypeptide sequence of SEQ ID NO:2. In another embodiment, a PRDT1 polypeptide comprises a polypeptide sequence with at least 50%, 60%, 70%, 80%, 85%, 90% or 95% or more sequence identity to a functionally active fragment of the polypeptide presented in SEQ ID NO:2, such as a SANT domain. In yet another embodiment, a PRDT1 polypeptide comprises a polypeptide sequence with at least 50%, 60%, 70%, 80%, or 90% identity to the polypeptide sequence of SEQ ID NO:2 over its entire length and comprises a SANT domain.

In another aspect, a PRDT1 polynucleotide sequence is at least 50% to 60% identical over its entire length to the PRDT1 nucleic acid sequence presented as SEQ ID NO:1, or nucleic acid sequences that are complementary to such a PRDT1 sequence, and may comprise at least 70%, 80%, 85%, 90% or 95% or more sequence identity to the PRDT1 sequence presented as SEQ ID NO:1 or a functionally active fragment thereof, or complementary sequences.

As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1990) 215:403-410; website at blast.wustl.edu/blast/README.html) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that hybridize to the nucleic acid sequence of SEQ ID NO:1. The stringency of hybridization can be controlled by temperature, ionic strength, pH, and the presence of denaturing agents such as formamide during hybridization and washing. Conditions routinely used are well known (see, e.g., Current Protocol in Molecular Biology, Vol. 1, Chap. 2.10, John Wiley & Sons, Publishers (1994); Sambrook et al., supra). In some embodiments, a nucleic acid molecule of the invention is capable of hybridizing to a nucleic acid molecule containing the nucleotide sequence of SEQ ID NO:1 under stringent hybridization conditions that comprise: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.2×SSC and 0.1% SDS (sodium dodecyl sulfate). In other embodiments, moderately stringent hybridization conditions are used that comprise: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a PRDT1 polypeptide can be produced. For example, codons may be selected to increase the rate at which expression of the polypeptide occurs in a particular host species, in accordance with the optimum codon usage dictated by the particular host organism (see, e.g., Nakamura Y et al, Nucleic Acids Res (1999) 27:292). Such sequence variants may be used in the methods of this invention.

The methods of the invention may use orthologs of the *Arabidopsis* PRDT1. Methods of identifying the orthologs in other plant species are known in the art. Normally, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, supra; Dieffenbach and Dveksler (Eds.) PCR Primer: A Laboratory Manual, Cold Spring Harbor Laboratory Press, NY, 1989). For instance, methods for generating a cDNA library from the plant species of interest and probing the library with partially homologous gene probes are described in Sambrook et al. A highly conserved portion of the *Arabidopsis* PRDT1 coding sequence may be used as a probe. PRDT1 ortholog nucleic acids may hybridize to the nucleic acid of SEQ ID NO:1 under high, moderate, or low stringency conditions. After amplification or isolation of a segment of a putative ortholog, that segment may be cloned and sequenced by standard techniques and utilized as a probe to isolate a complete cDNA or genomic clone. Alternatively, it is possible to initiate an EST project to generate a database of sequence information for the plant species of interest. In another approach, antibodies that specifically bind known PRDT1 polypeptides are used for ortholog isolation. Western blot analysis can determine that a PRDT1 ortholog (i.e., an orthologous protein) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt 11, as described in Sambrook, et al., supra. Once the candidate ortholog(s) are identified by any of these means, candidate orthologous sequence are used as bait (the "query") for the reverse BLAST against sequences from *Arabidopsis* or other species in which PRDT1 nucleic acid and/or polypeptide sequences have been identified.

PRDT1 nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., Methods Enzymol. (1991) 204:125-39), may be used to introduce desired changes into a cloned nucleic acid.

In general, the methods of the invention involve incorporating the desired form of the PRDT1 nucleic acid into a plant expression vector for transformation of in plant cells, and the PRDT1 polypeptide is expressed in the host plant.

An isolated PRDT1 nucleic acid molecule is other than in the form or setting in which it is found in nature and is identified and separated from least one contaminant nucleic acid molecule with which it is ordinarily associated in the natural source of the PRDT1 nucleic acid. However, an isolated PRDT1 nucleic acid molecule includes PRDT1 nucleic acid molecules contained in cells that ordinarily express PRDT1 where, for example, the nucleic acid molecule is in a chromosomal location different from that of natural cells.

Generation of Transgenic Plants with a PRDT1 Phenotype

PRDT1 nucleic acids and polypeptides may be used in the generation of transgenic plants having a modified pathogen resistance phenotype; in general, improved resistance phenotypes are of interest. Pathogenic infection may affect seeds, fruits, blossoms, foliage, stems, tubers, roots, etc. Accordingly, resistance may be observed in any part of the plant. In a preferred embodiment, altered expression of the PRDT1 gene in a plant is used to generate plants with increased resistance to *P. parasitica*. In a further preferred embodiment, plants that mis-express PRDT1 may also display altered resistance to other pathogens. Other oomycete pathogens of interest include *Pythium* spp, *Phytophthora* spp, *Bremia lactucae*, *Peronosclerospora* spp., *Pseudoperonospora. Sclerophthora macrospora*, *Sclerospora graminicola*, *Plasmopara viticola*, and *Albugo candidia*. Fungal pathogens of interest include *Alternaria brassicicola*, *Botrytis cinerea*, *Erysiphe cichoracearum*, *Fusarium oxysporum*, *Plasmodiophora brassica*, *Rhizoctonia solani*, *Colletotrichum coccode*, *Sclerotinia* spp., *Aspergillus* spp., *Penicillium* spp., *Ustilago* spp., and *Tilletia* spp. Bacterial pathogens of interest include *Agrobacterium tumefaciens*, *Erwinia tracheiphila*, *Erwinia stewartii*, *Xanthomonas phaseoli*, *Erwinia amylovora*, *Erwinia carotovora*, *Pseudomonas syringae*, *Pelargonium* spp, *Pseudomonas cichorii*, *Xanthomonas fragariae*, *Pseudomonas morsprunorum*, *Xanthomonas campestris*.

PRDT1 nucleic acids and polypeptides may also be used in the generation of transgenic plants having a modified, preferably an improved drought tolerance phenotype. Such plants may further display increased tolerance to other abiotic stresses, particular salt-stress and freezing, as responses to these stresses and drought stress are mediated by ABA (Thomashow, 1999 Annu. Rev1 Plant Physiol. Plant Mol. Biol 50: 571; Cushman and Bohnert, 2000, Curr. Opin. Plant Biol. 3: 117; Kang et al. 2002, Plant Cell 14:343-357; Quesada et al. 2000, Genetics 154: 421; Kasuga et al. 1999, Nature Biotech. 17: 287-291).

The methods described herein are generally applicable to all plants. Although activation tagging and gene identification is carried out in *Arabidopsis*, the PRDT1 gene (or an ortholog, variant or fragment thereof) may be expressed in any type of plant. In preferred embodiments, the invention is directed to crops including maize, soybean, cotton, rice, wheat, barley, tomato, canola, turfgrass, sugar beets, onions, beans, and flax. Other crops include alfalfa, tobacco, and other forage crops. The invention may also be directed to fruit- and vegetable-bearing plants, plants used in the cut flower industry, grain-producing plants, oil-producing plants, and nut-producing plants, among others.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to *Agrobacterium*-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising a PRDT1 polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.).

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature.

Expression (including transcription and translation) of PRDT1 may be regulated with respect to the level of expression, the tissue type(s) where expression takes place and/or developmental stage of expression. A number of heterologous regulatory sequences (e.g., promoters and enhancers) are available for controlling the expression of a PRDT1 nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the 35S CaMV (Jones J D et al, Transgenic Res (1992) 1:285-297), the CsVMV promoter (Verdaguer B et al., Plant Mol Biol (1998) 37:1055-1067) and the melon actin promoter (published PCT application WO0056863). Exemplary tissue-specific promoters include the tomato E4 and E8 promoters (U.S. Pat. No. 5,859,330) and the tomato 2AII gene promoter (Van Haaren M J J et al., Plant Mol Bio (1993) 21:625-640). In one preferred embodiment, PRDT1 expression is under the control of a pathogen-inducible promoter (Rushton et al., The Plant Cell (2002) 14:749-762). In another preferred embodiment, PRDT1 expression is under control of regulatory sequences from genes whose expression is associated with drought stress. For example, when the promoter of the drought stress responsive *Arabidopsis* rd29A gene was used to drive expression of DREB1A, *Arabidopsis* plants were more tolerant to drought, salt and freezing stress and did not have the stunted stature associated with plants over-expressing the DREB1A gene from the CaMV 35S promoter (Kasuga et al, 1999 Nature Biotech 17: 287). Promoters from other *Arabidopsis* genes that are responsive to drought stress, such as COR47 (Welin et al. 1995, Plant Mol. Biol. 29: 391), KIN1 (Kurkela and Franck, 1990, Plant Mol. Biol. 15: 137), RD22BP (Abe et al. 1997, Plant Cell 9, 1859), ABA1 (Accession Number AAG17703), and ABA3 (Xiong et al. 2001, Plant Cell 13: 2063), could be used. Promoters from drought stress inducible genes in other species could be used also. Examples are the rab17, ZmFer1 and ZmFer2 genes from maize (Bush et al, 1997 Plant J 11:1285; Fobis-Loisy, 1995 Eur J Biochem 231:609), the tdi-65 gene from tomato (Harrak, 2001 Genome 44:368), the His1 gene of tobacco (Wei and O'Connell, 1996 Plant Mol Biol 30:255), the Vupat1 gene from cowpea (Matos, 2001 FEBS Lett 491:188), and CDSP34 from *Solanum tuberosum* (Gillet et al, 1998 Plant J 16:257).

In yet another aspect, in some cases it may be desirable to inhibit the expression of endogenous PRDT1 in a host cell. Exemplary methods for practicing this aspect of the invention include, but are not limited to antisense suppression (Smith, et al., Nature (1988) 334:724-726; van der Krol et al., Biotechniques (1988) 6:958-976); co-suppression (Napoli, et al., Plant Cell (1990) 2:279-289); ribozymes (PCT Publication WO 97/10328); and combinations of sense and antisense (Waterhouse, et al., Proc. Natl. Acad. Sci. USA (1998) 95:13959-13964). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., Proc. Natl. Acad. Sci. USA (1988) 85:8805-8809), a partial cDNA sequence including fragments of 5' coding sequence, (Cannon et al., Plant Molec. Biol. (1990) 15:39-47), or 3' non-coding sequences (Ch'ng et al., Proc. Natl. Acad. Sci. USA (1989) 86:10006-10010). Cosuppression techniques may use the entire cDNA sequence (Napoli et al., supra; van der Krol et al., The Plant Cell (1990) 2:291-299), or a partial cDNA sequence (Smith et al., Mol. Gen. Genetics (1990) 224:477-481).

Standard molecular and genetic tests may be performed to further analyze the association between a gene and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing [VIGS, see Baulcombe D, (1999) Arch Virol Suppl 15:189-201]).

In a preferred application expression profiling, generally by microarray analysis, is used to simultaneously measure differences or induced changes in the expression of many different genes. Techniques for microarray analysis are well known in the art (Schena M et al., Science (1995) 270:467-470; Baldwin D et al., Cur Opin Plant Biol. (1999) 2(2):96-103; Dangond F, Physiol Genomics (2000) 2:53-58; van Hal N L et al., J Biotechnol (2000) 78:271-280; Richmond T and Somerville S, Curr Opin Plant Biol (2000) 3:108-116). Expression profiling of individual tagged lines may be performed. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with a PRDT1 Phenotype

The invention further provides a method of identifying plants that have mutations in endogenous PRDT1 that confer increased pathogen resistance and drought tolerance, and generating pathogen-resistant and drought-tolerant progeny of these plants that are not genetically modified. In one method, called "TILLING" (for targeting induced local lesions in genomes), mutations are induced in the seed of a plant of interest, for example, using EMS treatment. The resulting plants are grown and self-fertilized, and the progeny are used to prepare DNA samples. PRDT1-specific PCR are used to identify whether a mutated plant has a PRDT1 mutation. Plants having PRDT1 mutations may then be tested for the PRDT1 phenotype, or alternatively, plants may be tested for the PRDT1 phenotype, and then PRDT1-specific PCR is used to determine whether a plant having increased pathogen resistance and drought tolerance has a mutated PRDT1 gene. TILLING can identify mutations that may alter the expression of specific genes or the activity of proteins encoded by these genes (see Colbert et al (2001) Plant Physiol 126:480-484; McCallum et al (2000) Nature Biotechnology 18:455-457).

In another method, a candidate gene/Quantitative Trait Locus (QTLs) approach can be used in a marker-assisted breeding program to identify alleles of or mutations in the PRDT1 gene or orthologs of PRDT1 that may confer the PRDT1 phenotype (see Foolad et al., Theor Appl Genet. (2002) 104(6-7):945-958; Rothan et al., Theor Appl Genet (2002) 105(1):145-159); Dekkers and Hospital, Nat Rev Genet. (2002) January; 3(1):22-32). Thus, in a further aspect of the invention, a PRDT1 nucleic acid is used to identify whether a plant having increased pathogen resistance and/or drought tolerance has a mutation in endogenous PRDT1 or has a particular allele that causes the increased pathogen resistance and/or drought tolerance.

All publications cited herein are expressly incorporated herein by reference for the purpose of describing and disclosing compositions and methodologies that might be used in connection with the invention. All cited patents, patent applications, and sequence information in referenced websites and public databases are also incorporated by reference.

EXAMPLES

Example 1

Activation Tagging in Arabidopsis

Mutants were generated using the activation tagging "ACT-TAG" vector, pSKI015 (GI 6537289; Weigel D et al., 2000). Standard methods were used for the generation of Arabidopsis transgenic plants, and were essentially as described in published application PCT WO0183697. Briefly, T0 Arabidopsis (Col-0) plants were transformed with Agrobacterium carrying the pSKI015 vector, which comprises T-DNA derived from the Agrobacterium Ti plasmid, an herbicide resistance selectable marker gene, and the 4× CaMV 35S enhancer element. Transgenic plants were selected at the T1 generation based on herbicide resistance. T2 seed was collected from T1 plants and stored in an indexed collection, and a portion of the T2 seed was accessed for the screen.

Example 2

Pathogen Resistance Screen

Approximately 18 T2 seeds from each of the greater than 40,00 lines generated in Example 1, were planted in soil. The seed were stratified for three days and then grown in the greenhouse for seven days. The seedlings were inoculated with approximately $1 \times 10^5$ conidia per ml P. parasitica spores and incubated in a dew room at 18° C. and 100% humidity for 24 hours. The plants were then moved to a growth room at 20° C. and 60% relative humidity with ten-hour long light period for six days. Individual plants were evaluated for the presence or absence of conidiophores on cotyledons. Lines in which at least a single plant showed no conidiophore growth were re-tested in a secondary screen by releasing three sets of 18 seed and screening for resistance to P. parasitica growth as before.

Lines in which a significant number of plants showed no conidiophores after infection were subjected to a tertiary screen. Approximately 54 T2 seed were released, planted individually and infected with P. parasitica as before. The plants were evaluated for the number of conidiophores growing on a single cotyledon and ranked by the following scoring system: a score of 0 indicates 0 conidiophores per cotyledon, 1 indicates 1-5 conidiophores per cotyledon, 2 indicates 6-10 conidiophores per cotyledon, 3 indicates 11-20 conidiophores per cotyledon, and 4 indicates greater than 20 conidiophores per cotyledon The ACTTAG line designated W000058335 was identified as having an increased resistance phenotype. Specifically, 15.2% of individual plants showed no conidiophores in the secondary screen. In the tertiary screen, 31 plants scored as 0 (39.2%), 31 as 1 (39.2%), 4 as 2 (5.1%), 10 as 3 (12.7%) and 3 as 4 (3.8%). Control wild-type Col-0 plants were more susceptible; 36 plants scored 0 (7.6%), 21 as 1 (4.4%), 79 as 2 (16.6%), 250 as 3 (52.5%) and 90 as 4 (18.9%).

We performed standard molecular analyses, essentially as described in patent application PCT WO0183697, to determine the site of the T-DNA insertion associated with the increased pathogen resistance phenotype. Briefly, genomic DNA was extracted from plants exhibiting increased pathogen resistance. PCR, using primers specific to the pSKI015 vector, confirmed the presence of the 35S enhancer in plants from line W000058335, and Southern blot analysis verified the genomic integration of the ACTTAG T-DNA and showed the presence of a single T-DNA insertion in the transgenic line.

Plasmid rescue and inverse PCR were used to recover genomic DNA flanking the T-DNA insertion, which was then subjected to sequence analysis.

The sequence flanking the right T-DNA border was subjected to a basic BLASTN search and/or a search of the Arabidopsis Information Resource (TAIR) database (available at the arabidopsis.org website), which revealed sequence identity to BAC F22H5, (GI 12331602), mapped to chromosome 1. The junction of the left border of the T-DNA is at nt 20167 of F22H5, and the right border junction is at nt 20229. Sequence analysis revealed that the T-DNA had inserted in the vicinity (i.e., within about 10 kb) of the gene whose nucleotide sequence is presented as SEQ ID NO: 1 (GI 18410812 and GI 12331602, nucleotides 20955-21335) and which we designated PRDT1. Specifically, the right border was approximately 500 bp upstream of the start codon of SEQ ID NO: 1.

Example 3

Drought Tolerance Screen

Drought stress was imposed on transgenic plants generated in Example 1 by withholding water for 21-25 days. At this time the plants were beginning to bolt. From 6 to 10 days after the initiation of drought stress, observations of the plants were taken daily. Transgenic plants were compared to each other and wild-type control plants. Putative drought tolerant lines were identified as containing at least 2 plants that remained green and viable after wild-type plants had died or as plants that contained a soil moisture content of at least 50 mV (using a Delt-T Devices HH2 Soil Moisture Meter with a ML2× Theta Probe).

After drought tolerant lines were identified, water was applied to the plants to allow them to recover. When possible, T3 seed was collected from the plants. This T3 seed was then grown and the plants assessed for drought tolerant phenotype as described above.

The drought tolerant plants were then subjected to an "excised leaf transpiration test" in which seeds were planted, stratified, and grown for three weeks as described above. Then, either the entire rosette or a single leaf was excised and placed on a pre-weighed plastic weigh dish and left on the bench at room temperature. The mass of the plant material was recorded immediately after excision and at 30 min intervals afterward. The mass of drought tolerant plants often decreased less rapidly indicating that they were transpiring less rapidly.

To detect lines containing or lacking the insert, PCR analysis was performed using a set of DNA oligonucleotide primers; one that hybridizes to sequences in pSKI015, the other that hybridizes to sequences flanking the insert. Genotyping of individuals analyzed drought tolerance experiments indicated that plants containing the insert identified in plant line W000114956 were more tolerant of drought stress than plants without the insert.

The same methods described in Example 2 were used to determine the site of the T-DNA insertion associated with the increased pathogen resistance phenotype. Sequence analysis revealed that the T-DNA had inserted 423 base pairs from the start codon in At1g75250, which is the same gene that was responsible for the pathogen resistance phenotype of plant line W000058335, as described in Example 2.

Example 4

Analysis of *Arabidopsis* PRDT1 Sequence

The amino acid sequence predicted from the PRDT1 nucleic acid sequence is presented in SEQ ID NO:2 and GI 10092271. Sequence analyses were performed with BLAST (Altschul et al., 1997, J. Mol. Biol. 215:403-410), PFAM (Bateman et al., 1999), PSORT (Nakai K, and Horton P, 1999, Trends Biochem Sci 24:34-6), and CLUSTALW (Thompson J D et al, 1994, Nucleic Acids Res 22:4673-4680), among others. The PRDT1 protein has been characterized as a myb-related protein. PFAM analysis indicated a SANT DNA-binding domain at approximately amino acids 8-60.

The retroviral oncogene v-myb, and its cellular counterpart c-myb, encode nuclear DNA-binding proteins (Klempnauer and Sippel, 1987, EMBO J. 6: 2719-2725; Biednkapp et al. 1988, Nature 335: 835-837). These belong to the SANT domain family that specifically recognize the sequence YAAC(G/T)G (Aasland et al. 1996, Trends Biochem. Sci. 21:87-88). In myb, one of the most conserved regions consisting of three tandem repeats has been shown to be involved in DNA-binding.

Analysis using BLASTP or TBLASTN identified a number of related proteins and proteins predicted from nucleic acid (generally EST) sequences in other plant species. Related sequences, which are candidate orthologs, are presented in SEQ ID NOs 3-14 and descriptions from GenBank are provided below:

SEQ ID NO:3 translation, gi|887283|gb|L38243.1|L38243 BNAF0581E Mustard flower buds *Brassica rapa* cDNA-ORF 98aa *Brassica rapa*

SEQ ID NO:4 translation, gi|18459015|gb|BM437293.1|BM437293 VVA017C08_54081 An expressed sequence tag database for abiotic st 75aa *Vitis vinifera*

SEQ ID NO:5 translation, gi|15288211|gb|BI472102.1|BI472102 sah99e03.y1 Gm-c1050 *Glycine max* cDNA clone GENOME SYSTEMS CLONE 97aa *Glycine max*

SEQ ID NO:6 translation, gi|15258392|gb|BI433702.1|BI433702 EST536463 P. infestans-challenged leaf *Solanum tuberosum* cDNA clo 88aa *Solanum tuberosum*

SEQ ID NO: translation, gi|14492357|gb|BI071737.1|BI071737 C063P09U *Populus* strain T89 leaves *Populus tremula×Populus* trem 71aa P o SEQ ID NO:8 translation, gi|7981380|emb|CAB91874.1| (AJ277944) myb-related protein [*Lycopersicon esculentum*] 88aa *Lycopersicon esculentum*

SEQ ID NO:9 gi|5091605|gb|AAD39594.1|AC007858_8 (AC007858) 10A19I.9 [*Oryza sativa*] 126aa *Oryza sativa*

SEQ ID NO:10 gi|5091604|gb|AAD39593.1|AC007858_7 (AC007858) 10A19I.8 [*Oryza sativa*] 236aa *Oryza sativa*

SEQ ID NO:11 gi|18394750|ref|NP_564087.1|(NM_101808) myb-related protein, putative [*Arabidopsis thaliana*] 92aa *Arabidopsis thaliana*

SEQ ID NO:12 gi|15226604|ref|NP_179759.1|(NM_127736) unknown protein [*Arabidopsis thaliana*] gi|4567225|gb|AAD236 101aa *Arabidopsis thaliana*

SEQ ID NO:13 gi|15234999|ref|NP_195636.1|(NM_120086) putative protein [*Arabidopsis thaliana*] gi|7487341|pir||T08 97aa *Arabidopsis thaliana*

SEQ ID NO:14 gi|8778436|gb|AAF79444.1|AC025808_26 F18O14.26 [*Arabidopsis thaliana*]

SEQ ID NO:15 gi|20161824|dbj|BAB90739.1| [20161824] P0663E10.22 [*Oryza sativa (japonica* cultivar-group)]

SEQ ID NO:16 gi|19387259|gb|AAL87171.1|AF480496_25[19387259] putative myb-related protein [*Oryza sativa (japonica* cultivar-group)]

The predicted protein from an EST contig identified from *Lycopersicon esculentum* was also identified as an ortholog having 58% sequence identity to SEQ ID NO:2, and is presented as SEQ ID NO:17.

The translation of an EST contig from *Solanum tuberosum*, presented as SEQ ID NO:18, was identified as having 53% sequence identify to SEQ ID NO:1.

Example 5

Confirmation of Pathogen Resistance Phenotype/Genotype Association

PCR analysis, using primers to sequences in pSKI015 or flanking the insert, was used to detect lines containing or lacking the insert. W000058335 individuals analyzed in the tertiary screen were genotyped. Results indicated that plants that were homozygous or hemizygous for the insert were more resistant to *P. parasitica* infection than plants that were homozygous wild-type; 100% of the plants homozygous for the insert and 97% of the plants hemizygous for the insertion received resistance scores of 0 or 1 while only 31% of the wild-type segregants scored 0 or 1. These results suggest that the *P. parasitica* resistance trait in W000058335 is caused by the overexpression of PRDT1 and is inherited in a dominant manner RT-PCR analysis showed that the PRDT1 gene was over-expressed in plants from the line displaying the *P. parasitica* resistance phenotype. Specifically, RNA was extracted from tissues derived from plants exhibiting the resistance phenotype and from wild type COL-0 plants. RT-PCR was performed using primers specific to the sequence presented as SEQ ID NO:1, to other predicted genes in the vicinity of the T-DNA insertion (At1g75240, At1g75260, and At1g75270), and to a constitutively expressed actin (positive control). The results showed that plants displaying the PRDT1 phenotype over-expressed the mRNA for the PRDT1 gene, indicating the enhanced expression of the PRDT1 gene is correlated with the PRDT1 phenotype.

Example 6

Recapitulation of Pathogen Resistance Phenotype

The coding sequences of the PRDT1 gene were cloned behind the strong constitutive CsVMV promoter and transformed into wild-type Col-0 *Arabidopsis thaliana* plants. Primary transformants (T1 plants) were selected and allowed to go to seed. Seed from these plants were planted and evaluated for resistance to *Peronospora*.

Approximately 54 individual seedlings from twenty different primary transformants were planted, stratified and grown for 1 week in a growth chamber. The 1 week old seedlings were inoculated with *Peronospora* as described previously. After 1 week the seedlings were scored for *Peronospora* infection by counting the number of conidophores on a cotyledon. Plants with no conidophores on a cotyledon were scored 0, plants with 1-5 were scored 1, plants with 6-10 were scored 2, plants with 10-20 were scored 3 and plants with more than 20 conidophores on a cotyledon were scored 4. Wild-type Col-0 seedlings were included as a control. Six lines over-expressing PRDT1 were significantly more resistant to *Peronospora* than wild-type Col-0 plants. In the three most resistant lines, over 70% of the plants scored 0 or 1 while in wild-type Col-0 plants only 4% of the plants scored 0 or 1. These results indicate that over-expression of PRDT1 in wild-type Col-0 confers resistance to *Peronospora parasitica*.

Example 7

Confirmation of Drought Tolerance
Phenotype/Genotype Association

RT-PCR analysis showed that the PRDT1 gene was specifically overexpressed in plants from the line displaying the improved drought tolerance phenotype. Specifically, RNA was extracted from tissues derived from plants exhibiting the PRDT1 phenotype and from wild type COL-0 plants. RT-PCR was performed using primers specific to the sequence presented as SEQ ID NO:1 and to other predicted genes in the vicinity of the T-DNA insertion. The results showed that plants displaying the PRDT1 phenotype over-expressed the mRNA for the PRDT1 gene by about 500 fold compared to wild type plants, indicating that the enhanced expression of the PRDT1 gene is correlated with the PRDT1 phenotype.

Example 8

Recapitulation of the Drought Tolerant Phenotype

The coding sequences of the PRDT1 gene were cloned behind the strong constitutive CsVMV promoter and transformed into wild-type Col-0 *Arabidopsis thaliana* plants. Primary transformants (T1 plants) were selected and allowed to go to seed. Seed from these plants were planted and evaluated for drought tolerance.

Approximately 18 seed from 2 T2 populations (PRDT1-1 and PRDT1-2) transformed with the CsVMV::PRDT1 transgene were planted in soil in 4 inch pots. The seed were stratified at 4° C. for 3 days and then grown in the growth room for 4 weeks. Drought stress was imposed on the plants by withholding water 28 days after transfer to the growth room, at this time the plants were beginning to bolt.

Observations on every individual plant in each pot were made after the last watering (day 0), seven days after the last watering (day 7), fourteen days after the last watering (day 14) and seventeen days after the last watering (day 17). Plants that were fully turgid were scored 0, plants that showed slight wilting were scored 1, plants that showed significant wilting were scored 2 and plants that were fully desiccated were scored 3.

PRDT1-1 and PRDT1-2 plants were significantly more tolerant to drought than wild-type Col-0 plants. After seventeen days without water, Col-0 plants had an average score of 2.7 indicating that most plants were either significantly wilted or fully desiccated. However, the average score of PRDT1-1 and PRDT1-2 plants was 0.1 and 0.4 respectively. These scores indicate that most of the plants were fully turgid or slightly wilted. These results indicate that overexpression of PRDT1 confers a drought tolerant phenotype.

It is claimed:

1. A method of producing a plant having increased drought tolerance, said method comprising:
   a) introducing into cells of the plant a plant transformation vector comprising a nucleotide sequence that encodes a myb polypeptide that confers drought tolerance, said myb polypeptide selected from the group consisting of: the polypeptide sequence of SEQ ID NO:2, a polypeptide sequence having at least 95% sequence identity to SEQ ID NO: 2, and an *Arabidopsis thaliana* polypeptide having at least 85% sequence identity to SEQ ID NO: 2; and
   b) growing the transformed cells to produce a transgenic plant, wherein said nucleotide sequence is expressed, and said transgenic plant exhibits increased drought tolerance, relative to a control plant.

2. A transformed plant obtained by the method of claim 1.

3. A transformed plant part obtained from the plant according to claim 2.

4. The transformed plant of claim 2, wherein the nucleotide sequence is set forth in SEQ ID NO:1.

5. The transformed plant of claim 2, wherein the nucleotide sequence encodes an *Arabidopsis thaliana* myb polypeptide having at least 85% sequence identity to SEQ ID NO: 2.

6. The transformed plant of claim 5, wherein the *Arabidopsis thaliana* myb polypeptide has at least 90% sequence identity to SEQ ID NO: 2.

7. A method of producing a plant having increased drought tolerance, said method comprising:
   a) introducing into cells of the plant a plant transformation vector comprising a nucleotide sequence that encodes a drought tolerance polypeptide comprising the amino acid sequence of SEQ ID NO: 2 or SEQ ID NO: 13; and
   b) growing the transformed cells to produce a transgenic plant, wherein said nucleotide sequence is expressed, and said transgenic plant exhibits increased drought tolerance relative to a control plant.

8. A transformed plant produced by the method of claim 7.

9. The transformed plant of claim 8, wherein the nucleotide sequence encodes SEQ ID NO: 2.

10. The transformed plant of claim 9, wherein the nucleotide sequence comprises SEQ ID NO: 1.

11. The method of claim 1, wherein the transformation vector further comprises a constitutive promoter operably linked to the nucleotide sequence.

12. The method of claim 1, wherein the transformation vector further comprises a drought inducible promoter operably linked to the nucleotide sequence.

13. The transformed plant of claim 6, wherein the nucleotide sequence encodes an *Arabidopsis thaliana* myb polypeptide having at least 95% sequence identity to SEQ ID NO: 2.

* * * * *

UNITED STATES PATENT AND TRADEMARK OFFICE
CERTIFICATE OF CORRECTION

| | | |
|---|---|---|
| PATENT NO. | : 7,786,346 B2 | Page 1 of 2 |
| APPLICATION NO. | : 12/163394 | |
| DATED | : August 31, 2010 | |
| INVENTOR(S) | : Anderson et al. | |

It is certified that error appears in the above-identified patent and that said Letters Patent is hereby corrected as shown below:

Title Page, Item (56) OTHER PUBLICATIONS:

Page 1, right column, at Berrocal-Lobo et al., "Factor1in" should read --Factor1 in--.

Page 2, left column, at Lin et al., "ACO25814" should read --AC025814--.

Page 2, right column, at Weymann et al., "*Isd*" should read --*lsd*--.

In the Specification:

Column 2, line 51, "ability to a" should read --ability of a--.

Column 3, line 32, "useful the" should read --useful for the--.

Column 3, line 46, "more or the" should read --more of the--.

Column 3, line 62, "more or the" should read --more of the--.

Column 4, line 12, "more or the" should read --more of the--.

Column 7, line 17, "gt 11," should read --gt11,--.

Column 7, line 19, "orthologous sequence are" should read --orthologous sequences are--.

Column 7, line 28, "acid sequence may" should read --acid sequences may--.

Column 7, line 34, "of in plant," should read --of plant,--.

Column 7, line 38, "from least one" should read --from at least one--.

Column 7 line 58, "*Pseudoperonospora*." should read --*Pseudoperonospora* spp.,--.

Column 8, line 8, "particular salt-stress" should read --particularly salt-stress--.

Column 8, line 38, "bombardment calcium" should read --bombardment, calcium--.

Column 11, line 63, "cotyledon" should read --cotyledon.--.

Column 13, line 1, "analyzed drought" should read --analyzed in drought--.

Column 13, line 55, "NO: translation" should read --NO:7 translation--.

Signed and Sealed this

Thirteenth Day of September, 2011

David J. Kappos
*Director of the United States Patent and Trademark Office*

CERTIFICATE OF CORRECTION (continued)

U.S. Pat. No. 7,786,346 B2

Column 14, line 11, "26 F18014.26" should read --26 F18O14.26--.

Column 14, line 25, "sequence identify to" should read --sequence identity to--.

Column 14, line 44, "manner" should read --manner.--.

Column 15, line 8, "of conidophores on" should read --of conidiophores on--.

Column 15, line 12, "20 conidophores on" should read --20 conidiophores on--.

```
                        SEQUENCE LISTING

<160> NUMBER OF SEQ ID NOS: 18

<210> SEQ ID NO 1
<211> LENGTH: 381
<212> TYPE: DNA
<213> ORGANISM: Arabidopsis thaliana

<400> SEQUENCE: 1
atggcgtcaa actcaagaag ttcaatctca ccatggacgt ttagtcaaaa caagatgttc     60
gagagggcct tggcagttta cgacaaggac acacccgacc gatggcacaa tgtggcaaaa    120
gctgtcggag ggaaaactgt agaagaagtg aagcgccact atgacattct cgtcgaggat    180
ctcatcaaca tcgagactgg tcgtgtccct ttgcccaatt acaagacctt cgaatctaac    240
tcaagaagca tcaatgactt tgacacaagg tatataacta aatatctata tatgatgctc    300
tcgatatatt ttgataatca ttctagtgat tttgagaaat tctctcaaaa agttcttgta    360
agttatattt ctttggttta a                                              381

<210> SEQ ID NO 2
<211> LENGTH: 126
<212> TYPE: PRT
<213> ORGANISM: Arabidopsis thaliana
```

```
<400> SEQUENCE: 2

Met Ala Ser Asn Ser Arg Ser Ile Ser Pro Trp Thr Phe Ser Gln
1               5                   10                  15

Asn Lys Met Phe Glu Arg Ala Leu Ala Val Tyr Asp Lys Asp Thr Pro
            20                  25                  30

Asp Arg Trp His Asn Val Ala Lys Ala Val Gly Gly Lys Thr Val Glu
            35                  40                  45

Glu Val Lys Arg His Tyr Asp Ile Leu Val Glu Asp Leu Ile Asn Ile
50                  55                  60

Glu Thr Gly Arg Val Pro Leu Pro Asn Tyr Lys Thr Phe Glu Ser Asn
65                  70                  75                  80

Ser Arg Ser Ile Asn Asp Phe Asp Thr Arg Tyr Ile Thr Lys Tyr Leu
                85                  90                  95

Tyr Met Met Leu Ser Ile Tyr Phe Asp Asn His Ser Ser Asp Phe Glu
                100                 105                 110

Lys Phe Ser Gln Lys Val Leu Val Ser Tyr Ile Ser Leu Val
                115                 120                 125

<210> SEQ ID NO 3
<211> LENGTH: 98
<212> TYPE: PRT
<213> ORGANISM: Brassica rapa

<400> SEQUENCE: 3

Met Ala Ser Ser Ser Met Ser Ser Ser Trp Thr Ser Lys Gln Asn Lys
1               5                   10                  15

Ile Phe Glu Arg Ala Leu Ala Val Tyr Asp Lys Asp Thr Pro Asp Arg
            20                  25                  30

Trp Gln Asn Val Ala Lys Ala Val Gly Asn Lys Ser Ala Glu Glu Val
            35                  40                  45

Lys Arg His Tyr Asp Ile Leu Val Glu Asp Leu Met Asn Ile Glu Gln
50                  55                  60

Asp Leu Val Pro Leu Pro Lys Tyr Lys Thr Val Asp Val Gly Asn Lys
65                  70                  75                  80

Ser Arg Gly Ile Asn Gly Tyr Gly Leu Arg Leu Met Lys Asn Ile Glu
                85                  90                  95

Val Gln

<210> SEQ ID NO 4
<211> LENGTH: 75
<212> TYPE: PRT
<213> ORGANISM: Vitis vinifera

<400> SEQUENCE: 4

Met Ala Ser Thr Ser Leu Lys Ser Ser Gly Ser Trp Thr Pro Lys Gln
1               5                   10                  15

Asn Lys Leu Phe Glu Lys Ala Leu Ala Leu Tyr Asp Arg Asp Thr Pro
            20                  25                  30

Asp Arg Trp Gln Asn Val Ala Asn Ala Val Gly Gly Lys Ser Ala Glu
            35                  40                  45

Glu Val Lys Gln His Tyr Glu Ile Leu Ile Arg Asp Leu Lys His Ile
50                  55                  60

Glu Ser Gly Arg Val Pro Ile Pro Asn Tyr Lys
65                  70                  75

<210> SEQ ID NO 5
```

```
<211> LENGTH: 97
<212> TYPE: PRT
<213> ORGANISM: Glycine max

<400> SEQUENCE: 5

Met Glu Ser Cys Ser Ile Ser Ala Ser Gly Ser Trp Ser Val Lys Asp
1               5                   10                  15

Asn Lys Ala Phe Glu Lys Ala Leu Ala Val Tyr Asp Lys Asp Thr Pro
                20                  25                  30

Asp Arg Trp Tyr Asn Val Ala His Ala Val Gly Gly Lys Thr Pro Glu
            35                  40                  45

Glu Val Lys Arg His Tyr Glu Leu Leu Val Gln Asp Val Lys His Ile
 50                 55                  60

Glu Ser Gly Arg Val Pro Phe Pro Asn Tyr Lys Lys Thr Thr Ser Glu
65                  70                  75                  80

Ser Thr Asp Gln Glu Glu Lys Arg Leu Arg Asn Leu Asn Leu Asn Leu
                85                  90                  95

Gln

<210> SEQ ID NO 6
<211> LENGTH: 88
<212> TYPE: PRT
<213> ORGANISM: Solanum tuberosum

<400> SEQUENCE: 6

Met Ala Ser Ser Ser Leu Gln Ser Ser Ser Trp Thr Pro Gln Gln Asn
1               5                   10                  15

Lys Leu Phe Glu Arg Ala Leu Ala Gln Phe Asp Lys Asp Thr Pro Asp
                20                  25                  30

Arg Trp Gln Asn Val Ala Arg Ala Val Gly Gly Gly Lys Ser Ala Asp
            35                  40                  45

Glu Val Lys Arg His Tyr Glu Ile Leu Ile Glu Asp Leu Lys Arg Ile
 50                 55                  60

Glu Ser Gly Arg Val Pro Leu Pro Thr Tyr Thr His Glu Gln Gln Arg
65                  70                  75                  80

Leu Leu Arg Tyr Met Asn Leu His
                85

<210> SEQ ID NO 7
<211> LENGTH: 71
<212> TYPE: PRT
<213> ORGANISM: Populus tremula

<400> SEQUENCE: 7

Met Ser Ser Ser His Gln Thr Pro Arg Asn Ser Ser Ser Trp Thr
1               5                   10                  15

Pro Arg Glu Asn Lys Leu Phe Glu Lys Ala Leu Ala Leu Phe Asp Lys
                20                  25                  30

Asp Thr Pro Asp Arg Trp Lys Asn Val Ala Lys Ala Val Gly Gly Val
            35                  40                  45

Lys Ser Ala Glu Glu Val Lys Arg His Tyr Glu Ile Leu Ile Glu Asp
 50                 55                  60

Leu Lys His Ile Glu Pro Ala
65                  70

<210> SEQ ID NO 8
<211> LENGTH: 88
<212> TYPE: PRT
```

<213> ORGANISM: Lycopersicon esculentum

<400> SEQUENCE: 8

```
Met Ser Ser Met Ser Ser Gln His Gly Ser Ser Gly Ser Trp Thr Ala
1               5                   10                  15

Lys Gln Asn Lys Ala Phe Glu Lys Ala Leu Ala Val Tyr Asp Lys Glu
            20                  25                  30

Thr Arg Asp Arg Trp Ser Asn Val Ala Lys Ala Val Gly Gly Lys Thr
        35                  40                  45

Ala Glu Glu Val Lys Arg His Tyr Glu Ile Leu Leu Arg Asp Val Phe
    50                  55                  60

Phe Ile Asp Asn Gly Met Val Pro Phe Pro Lys Tyr Lys Thr Thr Gly
65                  70                  75                  80

Gly Ser His Asn Ser Thr Ser Asp
                85
```

<210> SEQ ID NO 9
<211> LENGTH: 126
<212> TYPE: PRT
<213> ORGANISM: Oryza sativa

<400> SEQUENCE: 9

```
Met Ala Ser Ala Ala Gly Ser Lys Gln Gln Ala Met Met Ser Leu
1               5                   10                  15

Pro Ser Ser Arg Gly Gly Gly Gly Gly Trp Thr Gln Arg Gln Asn
            20                  25                  30

Lys Gln Phe Glu Cys Ala Leu Ala Val Tyr Asp Lys Glu Thr Pro Asp
        35                  40                  45

Arg Trp His Asn Ile Ala Arg Tyr Met Gly Gly Ala Lys Ser Ala Asp
    50                  55                  60

Glu Val Arg Arg His Phe Asp His Leu Val Glu Asp Val Ser Arg Ile
65                  70                  75                  80

Glu Ser Gly Arg Val Pro Phe Pro Arg Tyr Ser Ser Ser Ser Ser
            85                  90                  95

Arg Gly Ala Asp Asp Gly Asn Arg Leu Leu Thr Val Phe His Leu Ser
            100                 105                 110

Ser Val Pro Arg Thr Arg Asn Ala Asn His Lys Phe Asn Thr
            115                 120                 125
```

<210> SEQ ID NO 10
<211> LENGTH: 236
<212> TYPE: PRT
<213> ORGANISM: Oryza sativa

<400> SEQUENCE: 10

```
Met Ala Gln Gln Ala Arg Ala Gln Trp Pro Gln Lys Gln Asn Lys Leu
1               5                   10                  15

Phe Glu Gln Ala Leu Ala Val Tyr Asp Lys Glu Thr Pro Asp Arg Trp
            20                  25                  30

His Asn Ile Ala Arg Ala Val Gly Gly Gly Lys Ser Ala Glu Asp Val
        35                  40                  45

Lys Arg Tyr Tyr Glu Met Leu Glu Glu Asp Ile Lys His Ile Glu Ser
    50                  55                  60

Gly Lys Val Pro Phe Pro Ala Tyr Arg Cys Pro Ala Ala Gly Tyr
65                  70                  75                  80

Gln Ala Glu Ser Arg Pro Ser Thr Ala Ala Glu Pro Ser Arg Leu Pro
            85                  90                  95
```

```
Leu Ser Asp Ser Gly Leu Ser Gly Ile Arg Pro Thr Gln Tyr Pro Pro
            100                 105                 110

Asp Gly Glu Leu Ser Pro Pro Arg His Arg Leu Arg Arg Gly Asn
        115                 120                 125

Gln Pro Ile Pro Ser Tyr Lys Pro Ser Pro Ser Arg Glu Gly Ile Phe
    130                 135                 140

Tyr Trp Glu Val Val Ala Ala Leu Lys Ser Arg Gly Thr Gly Ala
145                 150                 155                 160

Thr Ser Thr Pro Trp Ile Arg Leu Leu Pro Gly Leu Thr Val Cys
            165                 170                 175

Arg Leu Leu Gly Ser Ser Gly Cys Phe Asp Ala Trp Met Leu Ser Thr
            180                 185                 190

Ala Arg Leu Met Val Val Asn Thr Tyr Trp Met Ser Tyr Leu Thr Arg
            195                 200                 205

Ser Pro Glu Phe His Leu Asn Phe Pro His Ile Asn Leu Arg Lys Tyr
            210                 215                 220

Glu Val Val Cys Val Gln Pro Gly Phe Met Gln Glu
225                 230                 235

<210> SEQ ID NO 11
<211> LENGTH: 92
<212> TYPE: PRT
<213> ORGANISM: Arabidopsis thaliana

<400> SEQUENCE: 11

Met Ala Ser Ser Ser Met Ser Ser Ser Ser Trp Thr Ser Lys Gln
1               5                   10                  15

Asn Lys Met Phe Glu Arg Ala Leu Ala Val Tyr Asp Lys Asp Thr Pro
            20                  25                  30

Asp Arg Trp Gln Asn Val Ala Lys Ala Val Gly Ser Lys Ser Ala Glu
        35                  40                  45

Glu Val Lys Arg His Tyr Asp Ile Leu Val Glu Asp Leu Met Asn Ile
    50                  55                  60

Glu Gln Asp Leu Val Pro Leu Pro Lys Tyr Lys Thr Val Asp Val Gly
65                  70                  75                  80

Ser Lys Ser Arg Gly Ile Asp Asp Phe Asp Leu Arg
                85                  90

<210> SEQ ID NO 12
<211> LENGTH: 101
<212> TYPE: PRT
<213> ORGANISM: Arabidopsis thaliana

<400> SEQUENCE: 12

Met Ala Ser Gly Ser Met Ser Ser Tyr Gly Ser Gly Ser Trp Thr Val
1               5                   10                  15

Lys Gln Asn Lys Ala Phe Glu Arg Ala Leu Ala Val Tyr Asp Gln Asp
            20                  25                  30

Thr Pro Asp Arg Trp His Asn Val Ala Arg Ala Val Gly Gly Lys Thr
        35                  40                  45

Pro Glu Glu Ala Lys Arg Gln Tyr Asp Leu Leu Val Arg Asp Ile Glu
    50                  55                  60

Ser Ile Glu Asn Gly His Val Pro Phe Pro Asp Tyr Lys Thr Thr Thr
65                  70                  75                  80

Gly Asn Ser Asn Arg Gly Arg Leu Arg Asp Glu Glu Lys Arg Met Arg
                85                  90                  95
```

```
Ser Met Lys Leu Gln
            100

<210> SEQ ID NO 13
<211> LENGTH: 97
<212> TYPE: PRT
<213> ORGANISM: Arabidopsis thaliana

<400> SEQUENCE: 13

Met Ala Ser Ser Met Ser Ser Gln Ser Gly Ser Trp Thr Ala
1               5                   10                  15

Lys Gln Asn Lys Ala Phe Glu Gln Ala Leu Ala Thr Tyr Asp Gln Asp
                20                  25                  30

Thr Pro Asn Arg Trp Gln Asn Val Ala Lys Val Val Gly Gly Lys Thr
            35                  40                  45

Thr Glu Glu Val Lys Arg His Tyr Glu Leu Leu Val Gln Asp Ile Asn
        50                  55                  60

Ser Ile Glu Asn Gly His Val Pro Phe Pro Asn Tyr Arg Thr Ser Gly
65                  70                  75                  80

Gly Cys Thr Asn Gly Arg Leu Ser Gln Glu Lys Arg Tyr Val Leu
                85                  90                  95

Ser

<210> SEQ ID NO 14
<211> LENGTH: 639
<212> TYPE: PRT
<213> ORGANISM: Arabidopsis thaliana

<400> SEQUENCE: 14

Met Ala Ser Ser Met Ser Ser Ser Ser Trp Thr Ser Lys Gln
1               5                   10                  15

Asn Lys Met Phe Glu Arg Ala Leu Ala Val Tyr Asp Lys Asp Thr Pro
                20                  25                  30

Asp Arg Trp Gln Asn Val Ala Lys Ala Val Gly Ser Lys Ser Ala Glu
            35                  40                  45

Glu Val Lys Arg His Tyr Asp Ile Leu Val Glu Asp Leu Met Asn Ile
        50                  55                  60

Glu Gln Asp Leu Val Asn Glu Glu Tyr Glu Asn Pro Val Lys Leu Leu
65                  70                  75                  80

His Asp Val Lys Ile Ala Ile Cys Leu Arg Ile Gln Arg Asp Met Met
                85                  90                  95

Ala Lys Ile Ser Val Ala Val Leu Leu Ser Val Met Leu Leu Val Ser
                100                 105                 110

Ile Asn Ser Val Asp Ile Leu Ala Glu Glu Pro Thr Val Gly Gln
            115                 120                 125

Arg Val Asp Ser Ala Met Thr Ser Val Thr Asp Ala Phe Asn Glu His
        130                 135                 140

Gly Gly Pro Gln Ala Val Asp Thr Val Ser Ser Thr Phe Lys Ser Val
145                 150                 155                 160

Tyr Gly Trp Phe Gly Asp Lys Ala Lys Tyr Leu Glu Pro Ile Ser Ser
                165                 170                 175

Ser Cys Cys Ser Ser Ser Ser Ser Ser Gly Glu Glu Asn Thr Ala
                180                 185                 190

Ala Ala Asn Met Thr Glu Met Glu Ala Ala Glu Ala Leu Ala Asp Leu
            195                 200                 205
```

```
Ala Gln Leu Ala Ile Met Arg Glu Gln Val Phe Glu Ser Ala Ser
            210                 215                 220

Trp Gly Ser Lys Gly Lys Arg Val Arg Lys Val Lys Thr Glu Ser
225                 230                 235                 240

Pro Pro Ser Asp Ser Leu Leu Lys Pro Asp Ser Asp Thr Leu Pro
                245                 250                 255

Thr Pro Asp Leu Ala Glu Glu Arg Leu Val Lys Glu Glu Glu Glu
            260                 265                 270

Glu Glu Val Glu Pro Ile Thr Lys Glu Leu Thr Lys Ala Pro Val Lys
        275                 280                 285

Ser Glu Ile Asn Gly Glu Thr Pro Lys Pro Ile Leu Ala Ser Thr Leu
290                 295                 300

Ile Arg Cys Ser Arg Ser Asn Gly Cys Gly Arg Ser Arg Gln Asn Leu
305                 310                 315                 320

Ser Glu Ala Glu Arg Glu Arg Arg Ile Arg Arg Ile Leu Ala Asn
                325                 330                 335

Arg Glu Ser Ala Arg Gln Thr Ile Arg Arg Arg Gln Ala Met Cys Glu
                340                 345                 350

Glu Leu Ser Lys Lys Ala Ala Asp Leu Thr Tyr Glu Asn Glu Asn Leu
            355                 360                 365

Arg Arg Glu Lys Asp Trp Ala Leu Lys Glu Phe Gln Ser Leu Glu Thr
370                 375                 380

Ile Asn Lys His Leu Lys Glu Gln Val Leu Lys Ser Val Lys Pro Asp
385                 390                 395                 400

Thr Lys Glu Pro Glu Glu Ser Pro Lys Pro Ser Gln Val Glu Met Ser
                405                 410                 415

Thr Ser Ser Thr Pro Phe Tyr Phe Tyr Asn Gln Asn Pro Tyr Gln Leu
            420                 425                 430

Phe Cys Trp Pro His Val Thr Gln Ser Ser Asn Pro Met Ile Ser Pro
        435                 440                 445

Leu Glu Phe Pro Thr Ser Gly Gly Ala Ser Ala Lys Thr Ile Thr Thr
    450                 455                 460

Gln Glu His Glu Asn Ala Ala Asp Asp Asn Gly Gln Lys Thr His Phe
465                 470                 475                 480

Tyr Val Val Pro Cys Pro Trp Phe Leu Pro Pro Pro Asp His Ser Asn
                485                 490                 495

Gly Val Pro Phe Gly Leu Gln Asp Thr Gln Arg Gly Thr Phe Ser Asn
            500                 505                 510

Gly His His Ile Asp Asp Ser Ser Ala Arg Pro Met Asp Val Thr Glu
        515                 520                 525

Thr Pro Arg Ser His Leu Pro Thr Arg Ile Lys Glu Glu Asp Ser Gly
    530                 535                 540

Ser Pro Glu Thr Arg Pro Leu Tyr Asp Leu Asn Glu Ser Ala Thr Glu
545                 550                 555                 560

Val Leu Ser Glu Gly Gly Asp Gly Phe Pro Val Thr Gln Gln Ala Tyr
                565                 570                 575

Ser Leu Lys His Glu Asp Val Ser Glu Thr Thr Asn Gly Val Thr Leu
            580                 585                 590

Met Pro Pro Gly His His Val Leu Ile Ser Leu Pro Glu Lys Lys His
        595                 600                 605

Gly Ser Leu Ala Ala Ala Glu Ala Arg Lys Arg Arg Lys Glu Leu Thr
    610                 615                 620

Arg Leu Lys Asn Leu His Gly Arg Gln Cys Arg Met Gln Val Gly
```

```
                625                 630                 635

<210> SEQ ID NO 15
<211> LENGTH: 90
<212> TYPE: PRT
<213> ORGANISM: Oryza sativa

<400> SEQUENCE: 15

Met Ala Ser Met Ser Val Ser Ser Arg Ala Pro Gln Trp Thr Ala
1               5                   10                  15

Arg Gln Asn Glu Gln Phe Glu Arg Ala Leu Ala Val Tyr Asp Arg Asp
            20                  25                  30

Thr Pro Glu Arg Trp His Asn Ile Ala Arg Ala Val Ala Gly Lys Ser
        35                  40                  45

Ala Asp Glu Val Lys Leu Tyr Tyr Asp Leu Leu Val Glu Asp Val Lys
    50                  55                  60

Arg Ile Glu Thr Gly Lys Val Pro Phe Pro Ala Tyr Arg Cys Pro Gln
65                  70                  75                  80

Pro Ala Ile Ala Glu Asn Ser Gly Ile Trp
                85                  90

<210> SEQ ID NO 16
<211> LENGTH: 101
<212> TYPE: PRT
<213> ORGANISM: Oryza sativa

<400> SEQUENCE: 16

Met Ser Ser Ser Trp Thr Thr Lys Gln Asn Lys Val Phe Glu Arg Ala
1               5                   10                  15

Leu Ala Ile Tyr Asp Arg Asp Thr Pro Asp Arg Trp Gln Asn Val Ala
            20                  25                  30

Arg Ala Val Gly Gly Gly Lys Ser Val Asp Asp Val Lys Arg His Tyr
        35                  40                  45

Glu Lys Leu Ile Lys Asp Val Asp Arg Ile Asp Ser Thr Gly Gly His
    50                  55                  60

Gln Gly Ser His Tyr Asn Ser Ser Asn Ala Ser Ser Ser Ser Ser Ser
65                  70                  75                  80

Ser Ser Ser Asn Ser Arg Gly Ser Ala Asn Glu Asp Gln Arg Arg Arg
                85                  90                  95

Tyr His Asn Phe Gln
                100

<210> SEQ ID NO 17
<211> LENGTH: 97
<212> TYPE: PRT
<213> ORGANISM: Lycopersicon esculentum
<220> FEATURE:
<221> NAME/KEY: misc_feature
<222> LOCATION: (93)..(93)
<223> OTHER INFORMATION: Xaa can be any naturally occurring amino acid

<400> SEQUENCE: 17

Gln Lys Ile Ile Met Ser Ser Met Ser Ser Gln His Gly Ser Ser Gly
1               5                   10                  15

Ser Trp Thr Ala Lys Gln Asn Lys Ala Phe Glu Lys Ala Leu Ala Val
            20                  25                  30

Tyr Asp Lys Glu Thr Arg Asp Arg Trp Ser Asn Val Ala Lys Ala Val
        35                  40                  45

Gly Gly Lys Thr Ala Glu Glu Val Lys Arg His Tyr Glu Ile Leu Leu
```

-continued

```
                50                  55                  60
Arg Asp Val Phe Phe Ile Asp Asn Gly Met Val Pro Phe Pro Lys Tyr
65                  70                  75                  80

Lys Thr Thr Gly Gly Ser His Asn Ser Thr Ser Asp Xaa His Tyr Phe
                85                  90                  95

Tyr

<210> SEQ ID NO 18
<211> LENGTH: 732
<212> TYPE: DNA
<213> ORGANISM: Solanum tuberosum

<400> SEQUENCE: 18
agtaatggca tcaagctcac ttcaatcttc atcatggaca ccgcagcaaa acaagttatt      60
tgaaagggca ctagctcaat tcgataagga cacacctgac cggtggcaga atgtggcgcg     120
ggcggttgga ggtggaaaat ccgccgatga agtaaagaga cactatgaaa tacttattga     180
ggatctcagg cgcattgaat ctggacgtgt tcctcttcct acttacaccc atgaacaaca     240
aaggtattct taatcattct ctttaagtct tttgtccgtt attatttaaa attacaacat     300
tcaaaagttc tttcaaattc aattggatgg agtgaataaa tatgatattt tttgtttcaa     360
aggaatagca aagtatatat actttgatct tgaacatttt gaaatgtgaa atgagacggt     420
tccatactta aaccctactt tactagtcta tacttttgaa tgagacagtt acatatttct     480
aacttttgtc tatttgtaaa acataagaaa tattcttatc ttttttagaa ttcagttaat     540
attttctttt caacctttg ttgtatttta gtcgattcga gtcatgcaaa cagttcggat      600
atgaatgaaa tttagaaatc ttaaatttca taaattaaca aaacagacat ggtgcggtgt     660
ttgaaagtta ttgcatgtaa ccctataccc tattctaatt aagagtcctt aaatctttat     720
tagtatcttt tt                                                         732
```